US007128705B2

(12) United States Patent
Brendley et al.

(10) Patent No.: US 7,128,705 B2
(45) Date of Patent: Oct. 31, 2006

(54) MOTION-COUPLED VISUAL ENVIRONMENT FOR PREVENTION OR REDUCTION OF MOTION SICKNESS AND SIMULATOR/VIRTUAL ENVIRONMENT SICKNESS

(75) Inventors: Keith W. Brendley, McLean, VA (US); Jed Marti, Salt Lake City, UT (US)

(73) Assignee: Artis LLC, McLean, VA (US)

( * ) Notice: Subject to any disclaimer, the term of this patent is extended or adjusted under 35 U.S.C. 154(b) by 437 days.

(21) Appl. No.: 10/304,060

(22) Filed: Nov. 26, 2002

(65) Prior Publication Data
US 2004/0102676 A1 May 27, 2004

(51) Int. Cl.
*A61M 21/00* (2006.01)
(52) U.S. Cl. .......................... 600/27; 702/150; 348/148
(58) Field of Classification Search ............ 600/27–28; 702/150–154; 128/897–898; 340/945, 967, 340/973–978; 348/148; 701/1, 3, 23
See application file for complete search history.

(56) References Cited

U.S. PATENT DOCUMENTS

| | | | |
|---|---|---|---|
| 4,576,184 A | 3/1986 | Westerman | |
| 4,925,878 A | 5/1990 | Bodo et al. | |
| 5,042,910 A | 8/1991 | Dolezal | |
| 5,067,941 A | 11/1991 | Hendricks | |
| 5,629,848 A | 5/1997 | Repperger et al. | |
| 5,647,835 A | 7/1997 | Martineau | |
| 5,694,939 A | 12/1997 | Cowings | |
| 5,829,446 A | 11/1998 | Tiffany | |
| 6,042,533 A | 3/2000 | Kania | |
| 6,050,822 A | 4/2000 | Faughn | |
| 6,228,021 B1 | 5/2001 | Kania | |
| 6,234,953 B1 | 5/2001 | Thomas et al. | |
| 6,497,649 B1 | 12/2002 | Parker et al. | |
| 6,692,428 B1 | 2/2004 | Kania | |
| 6,866,225 B1 * | 3/2005 | Jones et al. ............... 244/118.5 |
| 2001/0000459 A1 | 4/2001 | Kania | |

OTHER PUBLICATIONS

Mocove—Motion Coupled Virtual Environment, Marti et al; Sep. 13, 2002; www.artisllc.com; pp. 1-17.*
Lexus brochure; Apr. 30, 2002; www.lexus.com; pp. 1-4.*
Alexander S.J., Cotzin M., Hill C., Riccuiti E., Wendt, G. (1945), Wesleyan University studies of motion sickness: 1. The effects of variations of time intervals between accelerations upon sickness rates, J Psychol. 19: 49-62.
Brandt, Th., Wist, E.R., Dichgans, J. (1975), Foreground and background in dynamic spatial orientation, Percept. Psychophys. 17: 497-503.
Brendley, K.W., Cohn, J., Marti, J., Muth, E., and Stripling, R. (2003), Using Motion-Coupled Visual Environments to Control Motion Sickness, Proceedings of Aerospace Medical Association (AsMA), San Antonio, TX.

(Continued)

*Primary Examiner*—John P. Lacyk
(74) *Attorney, Agent, or Firm*—Nixon & Vanderhye P.C.

(57) ABSTRACT

A motion-coupled visual environment prevents, reduces and/or treats motion sickness by sensing inertial motion and providing a corresponding evocative image for a subject to view. Inertial sensors may include accelerometers, gyroscopes or a variety of other different sensor types. A cross-coupling algorithm may be used to cross couple different sensed inertial motions. A variety of mapping schemes may be used to map sensed inertial motion to corresponding motion within the evocative scene displayed on the display. Applications include reducing motion sickness on passenger vehicles such as airplanes, trains and cars; on military vehicles such as ships, airplanes, helicopters and the like; and reducing "cybersickness" in the context of simulations on moving platforms.

17 Claims, 11 Drawing Sheets

OTHER PUBLICATIONS

Brendley, K.W., (2003), Reducing Motion Sickness with MOCOVE, Dawnbreaker Conf., Reston, VA.

Brendley, K.W., Cohn, J.V., Marti, J., Bender, G., Muth, E., & Stripling, R. (2003), Controlling Motion Sickness with Motion-Coupled Visual Environments, Proceedings of the ASNE Human Factors Symposium, Washington, DC.

Cohn, J.V., Allen, R., Brendley, K., Stanney, K, Muth, E. & Schmorrow, D. Shiphandling Applications for Virtual Environment Simulation, in D. Vincenzi (ed): (book chapter in submission).

Cohn, J., Muth, E., Schmorrow, D., Brendley, K. and Hillson, R. (2002), Reducing Negative Effects from Virtual Environments: Implications for Just-In-Time Training (Presented at NATO Human Factors and Medicine Symposium on Spatial Disorientation in Military Vehicles: Causes, Consequences and Cures, La Caruna, Spain).

Dichgans J. Brandt Th. (1978) Visual-vestibular interactions: effects on self-motion perception and postural control. In Handbook of Sensory Physiology. vol. 8. Perception (RH Held, H Leibowitz and H-L Teuber Eds.), Springer-Verlag: New York, 755-804.

DiZio P., Lackner, J.R. (1992) Spatial orientation, adaptation, and motion sickness in real and virtual environments. Presence, 1, 319-328.

DiZio, P. and Lackner, J.R. (1991), Motion sickness susceptibility in parabolic flight and velocity storage activity, Aviation, Space, and Environmental Medicine, 62, 300-307.

Graybiel, A. and Lackner, J.R. (1980), A sudden stop vestibulovisual test for rapid assessment for motion sickness manifestations, Aviation, Space, and Environmental Medicine, 58:21-23.

Graybiel, A., Wood, C.D., Miller, E.F. and Cramer, D.B. (1968), Diagnostic criteria for grading the severity of acute motion sickness, Aerospace Med., 39: 453-455.

Guignard, J.C. and McCauley, M.E. (1982), Motion sickness incidence induced by complex periodic waveforms, Aviation Space and Environmental Medicine, 53: 554-563.

Hill, J. (1936), The care of the seasick, Brit Med J, Oct.-Dec.: 802-807.

Kennedy, R.S., Hettinger, L.J. and Lilienthal, M.G. (1990) Simulator Sickness. In G.H. Crampton (Ed.), Motion and Space Sickness, (pp. 317-342). Boca Raton, Fl: CRC Press.

Kennedy, R.S., Lane N.E., Berbaum, D.K. and Lilienthal, M.G. (1993), Simulator sickness questionnaire: An enhanced method for quantifying simulator sickness, Int'l J Aviat Psychol, 3: 203-220.

Kennedy, R.S., Tolhurst, G.C. and Graybiel, A. (1965), The effects of visual deprivation on adaptation to a rotating room, Naval School of Aviat Med, Pensacola FL: NSAM-918.

Lawther, A. and Griffin, M.J. (1986), The motion of a ship at sea and the consequent motion sickness amongst passengers, Ergonomics, 79: 535-552.

Lawther, A. and Griffin, M.J. (1987), Prediction of the incidence of motion sickness from the magnitude, frequency and duration of vertical oscillation, Journal of Acoustical Society of America, 82: 957-966.

Money, K.E. (1970), Motion sickness, Physiol Rev, 50: 1-39.

O'Hanlon, J.F. and McCauley, M.E. (1974), Motion sickness incidence as a function of the frequency and acceleration of a vertical sinusoidal motion, Aerospace Medicine, 45, 366-369.

Reason, J.T. and Brand, J.J. (1975), Motion sickness, London: Academic Press.

Stanney, K.M and Salvendy, G. (1998), Aftereffects and sense of presence in virtual environments: Formulation of a research and development agenda, International Journal of Human-Computer Interaction, 10(2), 135-187.

Stripling, R., Cohn, J., Muth, E., Balaban, C., Hillson, R. and Brendley, K.W., Control strategies for reducing motion sickness, Proceedings of Society for Neuroscience, 2003, New Orleans.

Archived Web Page, D. Maxwell, "Multi-Modal Motion Effects" ("Date Last Modified Jul. 5, 2001").

Archived Web Page, ArtisIncLLC (purportedly from Mar. 31, 2001).

\* cited by examiner

MOTION-COUPLED VISUAL ENVIRONMENT FOR PREVENTION OR REDUCTION OF MOTION SICKNESS AND SIMULATOR/VIRTUAL ENVIRONMENT SICKNESS

CROSS-REFERENCES TO RELATED APPLICATIONS

Not applicable.

STATEMENT REGARDING FEDERALLY SPONSORED RESEARCH OR DEVELOPMENT

Not applicable.

FIELD OF THE INVENTION

The present invention relates to the prevention or reduction of motion sickness by creating a motion concordant visual environment.

BACKGROUND AND SUMMARY OF THE INVENTION

Countless trips and vacations have been spoiled by motion sickness. Motion sickness symptoms range from the distracting, such as eyestrain and blurred vision, to the debilitating, such as nausea, depression and apathy. Moreover, motion sickness generally does not go away immediately upon removal of the stimulus making the person sick, but rather takes some time to subside These symptoms often cause inconvenience and discomfort, and may in some instances cause more serious issues. Imagine for example a motion-sick soldier who must function effectively in combat immediately after being transported by airplane, ship or helicopter.

Motion sickness most notably occurs in automobiles, trucks, military vehicles, ships, airplanes, and other motion sources. Some people get motion-sickness every time they ride in a car, on a plane or in a ship. But interestingly, motion sickness is not limited to situations where there is actual motion. For example, one may get motion sickness while stationary if exposed to large format immersive displays such as commonly employed by simulators, virtual environments (VE), high-definition television, military displays and other display systems. Motion sickness due to simulator and virtual-environment exposure is commonly referred to as "cybersickness." One may also suffer motion sickness if exposed to a large format display that, itself, is on a moving platform. This can occur for example with a training simulation on a ship, an Unmanned Aerial Vehicle (UAV) operator control station on an aircraft, or possibly even under some circumstances while watching an immersive television display in a moving car, plane or train.

Cybersickness occurs in a high percentage of individuals receiving virtual training. Given sufficient stimulation, motion sickness can be induced in all individuals with intact senses of balance. Virtual-environment exposure aftereffects include eyestrain, dizziness, and nausea, which can last more than an hour after a training session. In a significant percentage of the population, symptoms can persist for more than six hours post session. Prolonged exposure to virtual-environment simulations can lead to distinct physiological changes, such as in the resting point of accommodation or recalibration of perception-action couplings.

Common approaches for reducing or relieving motion sickness consist primarily of medications and alternative health products. Examples include Dramamine, Scopolamine, herbal remedies, and pressure bands worn on the wrist. Most medications for motion sickness have undesirable side effects such as drowsiness, and the efficacy of alternative health products has not been proven in clinical trials. Additionally, to be effective, medications such as Dramamine usually require ingesting before the onset of motion-sickness. This may not help a passenger who unexpectedly gets motion-sickness.

Discord of spatial information from the principal spatial senses (vestibular system, eyes, and non-vestibular proprioceptors) has been shown to be among the primary causes of motion sickness. This condition of sensory discordance, where one's spatial sensors are in conflict, is commonly experienced when the inertial environment is not correctly reflected by the visual environment. The visual stimuli do not match the proprioceptive receptors, including the vestibular system—or in simpler terms, the motion the body senses does not match the motion seen by the eyes.

The discontinuity between actual motion and perceived motion in a virtual environment has also been shown to be among the contributing factors to cybersickness. This decoupling can arise from a mismatch between visually presented scene motion and physically experienced motion. New research indicates that an environment that has a display on an independent motion platform is even more provocative in causing motion sickness.

Some in the past have tried to use a sensor and a display to reduce motion sickness.

One approach uses an "artificial labyrinth" displayed on a head-mounted display in conjunction with motion sensors mounted to the head and body to alleviate motion sickness. In this approach, motion sensors or a video recorder are mounted the user's head to provide body, head and inertial environment motion signals indicating the user's true orientation and motion correspond to the user's proprioceptive senses. A series of visual cues, such as lines that behave similar to attitude indicators found in airplanes, are presented to the user in the form of "artificial labyrinth" visual stimuli displayed on the head-mounted display (HMD). For example, the user is presented with a line that relates to the orientation of his or her head and body and also to the inertial platform on which the user is stationed. Another approach presents a stabilized image to the user in place of the actual image one would normally perceive. This similar to how motion picture cameras works. The motion sensor data or video images are averaged to provide a smooth stabilized cue or image, but the stabilized image is not aligned to the actual inertial environment. Thus the presented image is stabilized but it is unrelated to motion in the physical world. Such a stabilized but uncoupled image may actually abet the onset of motion sickness rather than abating it. Exposure to an uncoupled visual environment and inertial environment may in some cases produce significantly more severe sickness than exposure to just the virtual environment or just the motion platform.

Another approach uses a sensor and a sensor converter to translate inertial motions into perceptual indications, namely:

1) audible tones of varying frequency and volume,
2) mechanical vibrations or forces along different parts of the body, or
3) visual shapes of different color and size.

With this approach, one will often find the sensors are head mounted, object mounted, or in the case of a virtual environment, information is extracted directly from the simulation. Based on this sensed motion, the user would receive audio and/or mechanical and/or visual stimulation.

For audio feedback, the user would receive a different frequency tone that would vary in spectral emphasis based on the motion sensed. However, we have found no human subject research in the open, scientific literature that supports this approach for alleviating motion sickness. The working theory, apparently, is that one may introduce different audible tones and volumes that counteract mechanisms in the vestibular system that lead to motion sickness. It is unclear what these mechanisms may be or how they would be controlled.

For mechanical feedback, the prior approach envisions a device such as a wristband that would vibrate in response to sensed inertial motion. Again, it is not clear how this would resolve the discordance in sensory information between visual and proprioceptive receptors.

For the visual feedback of this prior approach, the display may consist of different shapes, size and colors that vary in some manner based on the inertial frame of reference. For instance, the color of a square could become darker or lighter depending on the sensed pitch. In addition, these elements could be displayed in columns or rows which could be made to appear to be moving with respect to a sensed motion. Once again, it is unclear how such a display would function or whether it would succeed in reducing motion sickness.

Another feedback approach consists of sensing the motion of an individual and then processing the signal to correspond to the actual motion that the vestibular system experiences. Based on these processed signals, an independent visual background (IVB) would be presented to the user. Generally, the independent visual background would consist of visual cues such as an array of vertical and horizontal lines. Since motion of the individual is be sensed, the device appears to be limited to simulators and virtual environments in stationary environments.

This prior approach envisions the user seeing an independent visual background superimposed upon the image. In the case of a virtual environment or non-moving simulator, the independent visual background would consist of a pattern of stationary lines. So while the scene may include motion, the visual cues that make up the independent visual background would correspond to the vestibular system and show no motion. It is well known in the field of virtual environments that less immersive environments tend to generate less motion sickness. By interrupting the scene with a clearly visible grid pattern superimposed upon the virtual sky or walls, the immersive effect of the virtual environment is curtailed, thus reducing the level of motion sickness.

The inverse of this would be when one is experiencing motion but the visual cues present none, such as when one is in the interior of the ship without windows. In this case, the independent visual background would be a pattern of lines that would move in such away as to correspond to the motion felt by the vestibular system. This independent visual background could be displayed via projector, head mounted display, or other method.

One drawback of this approach is that a grid of lines may be insufficient to cause the visual system to orient to the grid as opposed to the environment in the room. What the user will see will be a grid pattern moving along a wall. This is similar to the artificial labyrinth approach discussed earlier. In both cases, however, it seems unlikely that users will perceive the line patterns as representing a visual environment with which to orient themselves. If the presented visual stimuli do not "draw the user in," then efficacy is in question.

Another potential drawback of this prior approach is that these cues could interfere with whatever tasks one is performing. This would especially be true for the independent visual background, which overlays a grid of lines on what is visually perceived.

Thus, while much work has been done in the past, no one has yet developed a truly effective display-based technology for reducing, eliminating or alleviating motion sickness. Such technology would be very desirable for use in a wide range of applications including for example military vehicles, passenger vehicles, and stationary and moving simulation platforms.

The present invention solves these problems by providing a new kind of motion coupled visual environment that can be used to prevent, reduce and treat motion sickness. One preferred exemplary illustrative embodiment couples physically indicated motion of the inertial environment to motion of a visually presented scene. This coupling alleviates the discord of spatial information from the principal spatial senses such as visual, vestibular and other proprioceptive receptors.

One possible illustrative arrangement, for example, is to display the cockpit view of an aircraft moving over terrain on a computer display. This display is presented on a motion platform that is independent of the display such as a ship at sea, an automobile in motion or many other platforms. Inertial and other types of sensors record motion information, and aspects of this information are fed back into the computer display. For example, a sensed heave (vertical motion) may be shown as a slight pitch or a roll of ten degrees may be shown as a roll of two degrees. Various algorithms may be used to map motion into display information are possible. The user then simply views the display, which will prevent, reduce or at least delay onset of motion sickness for healthy individuals and will even relieve motion sickness for users that are already symptomatic.

A motion coupled visual environment reduces the incidence and severity of motion sickness as compared with exposure to an inertial environment alone. This reduction in motion sickness may be significant. One example illustrative implementation of a motion-coupled visual environment generator includes four components:

an inertial sensor,
a visual display,
software for processing the sensor information, and
software for modifying the visual display.

The exemplary illustrative arrangement works by sensing the inertial environment and relaying this information to an evocative visual scene. For example, one non-limiting example of an evocative scene is a ship moving over a textured water surface with a highly textured mountainous background surrounding the water. Many other scenes are possible. In example arrangements, the scene is modified to coincide fully or partially with the inertial environment, or the visual environment may map onto the inertial environment in a more complex manner. Coupling the visual and inertial environments with a one-to-one mapping of as little as 10% (where the visually represented pitch, for example, is only 10% the magnitude of the actual pitch) may still produce statistically significant beneficial results, although many other successful mapping schemes are possible. In addition, it is possible but not necessary to match the direction of all inertial motions. For example, presenting a visual heave and pitch is generally more effective than presenting a visual heave alone even though the inertial stimuli may include only heave motion.

Generally, we have found that a visual scene is most effective in alleviating or treating motion sickness if it serves to visually entrain the user. While cues may tell the user what is occurring in the inertial environment, they generally do not alleviate the discord perceived by the spatial senses. For example, the presence of an attitude indicator in the cockpit of an aircraft does not prevent a pilot from becoming motion sick. Simply knowing one's position relative to the Earth's frame of reference is generally insufficient information to recouple discordant visual and proprioceptive environments. The user preferably visually tracks stimuli that indicate some correspondence with the inertial frame of reference. Such a stimulus may be produced for example via a virtual scene such as a ship moving over the water; alternatively, it could simply be a window of text moving relative to the desktop or any other type of visual display.

In one preferred illustrative embodiment, the presented scene creates apparent motion. Since motion sickness is caused by the discordance between visual stimuli and inertial stimuli as sensed by proprioceptive receptors, among other causes, the visual scene is preferably sufficiently evocative to overcome the perceived discordance. In general, the more realistic and believable the visual scene, the more evocative it becomes, but there are exceptions to this general rule. Effective visual scenes are generally those that can impart a sense of motion to the viewer. Examples include a realistic scene such as those generated by a simulation or virtual environment, or a visual flow field such as that of a "star field" that is moving towards the user. Current technologies for presenting visual information include cathode ray tubes (CRT), flat panel displays, head mounted displays (HMDs), holographic displays and other technologies.

Motion coupled virtual environments can be placed on independent motion environments such as a car, ship, airplane or other motion platform. Motion sickness induction on these platforms is generally greatest when visual access to the inertial environment is limited either physically or perceptually. Physical restrictions could, for example, include a car at night, the rear of aircraft with no windows, or the bowels of a ship with no portals. Perceptual restrictions could include, for example, reading an electronic book in a car, watching a video in an aircraft, or operating an instrument aboard a ship. Here, the outside scene may be available, but the user's attention is diverted to operations within the interior.

Motion sickness can also occur even if the user has good visibility of the external environment and is not distracted from viewing it. Proprioceptive receptors are oftentimes poor at judging the true motion of the inertial environment. Thus, a visual scene that corresponds with the inertial environment may still disagree with the proprioceptive receptors. Another method for motion sickness to occur even with good visual contact with the environment is when the viewpoint is far removed from the most readily apparent visual cue. This may happen in an aircraft, for example; the aircraft may heave in the vertical direction by many feet at a rate that is highly evocative, and yet if the aircraft is at a great enough altitude, the visually presented scene can only barely be perceived to move. Another example would be of an aircraft moving over terrain at low altitude. Suppose a passenger is able to view the terrain through a portal in the floor. He or she would see the terrain moving past the portal at great speed, but the body of the passenger would feel at rest within the stable aircraft. This can create a dissonant visual and inertial environment and thus motion sickness. There are many more examples of this type. In all of these cases, it would be better for those within the motion environment to train their attention on an appropriate motion-coupled visual environment display or displays in order to relieve the onset of motion sickness.

A further preferred exemplary embodiment provides a method for alleviating motion sickness caused by a motion environment and by a visual environment operating within an uncoupled inertial environment, such as one would find with a training simulator used aboard a ship and in many other situations. In one exemplary instantiation, through the use of inertial sensors and visual scene data, the visually presented motion and the physically indicated motion of the individual is sensed. These signals are then processed and conditioned to better correlate with the proprioceptive senses, and an evocative environment is presented to the individual that harmonizes the visual and proprioceptive senses associated with motion.

Example non-limiting advantageous features and advantages provided by an illustrative exemplary embodiment include:

senses the inertial environment and couples selected aspects of this environment into an evocative visual scene that, when viewed, reduces the onset and severity of motion sickness.

senses the inertial environment and couples selected aspects of this environment into an evocative visual scene that, when viewed, treats motion sickness by reducing the discordance between the visual and inertial environments.

may be used with a virtual environment or simulation whose primary purpose is not the reduction of motion sickness. In this case, the arrangement senses the inertial environment and couples selected aspects of this environment into the visual scene within the virtual environment or simulation that, when viewed, reduces the onset and severity of motion sickness, simulator sickness, cyber-sickness or any combination of these and other related illnesses.

may be used with a display of video information such as a radar screen display, a commercial television display, a window of text such as in a work processor or electronic book, static or motion graphics or any other type of electronic display and information that may be shown on such a display. In this case, the arrangement senses the inertial environment and couples selected aspects of this environment to move either the entire display image or some window within the display such that, when viewed, it reduces the onset and severity of motion sickness.

may be calibrated to match inaccurate tendencies in a subject's proprioceptive receptors using motion tests prior to use, thus making it even more effective in reducing or alleviating motion sickness.

may permit the user to calibrate on-the-fly the degree and extent of coupling between the sensed inertial environment and the presented visual environment, thus increasing is effectiveness in reducing or alleviating motion sickness.

will permit physiological and other data from the user to be recorded that give independent indications of motion sickness, and these data will be used to calibrate the degree and extent of coupling between the inertial environment and presented visual scene, thus increasing the device's effectiveness in reducing or alleviating motion sickness.

BRIEF DESCRIPTION OF THE DRAWINGS

These and other features and advantages provided in accordance with presently preferred exemplary embodiments of the invention will be better and more completely understood by referring to the following detailed description in connection with the drawings, of which.

DETAILED DESCRIPTION OF PRESENTLY PREFERRED EXAMPLE ILLUSTRATIVE EMBODIMENTS

Figure 1:
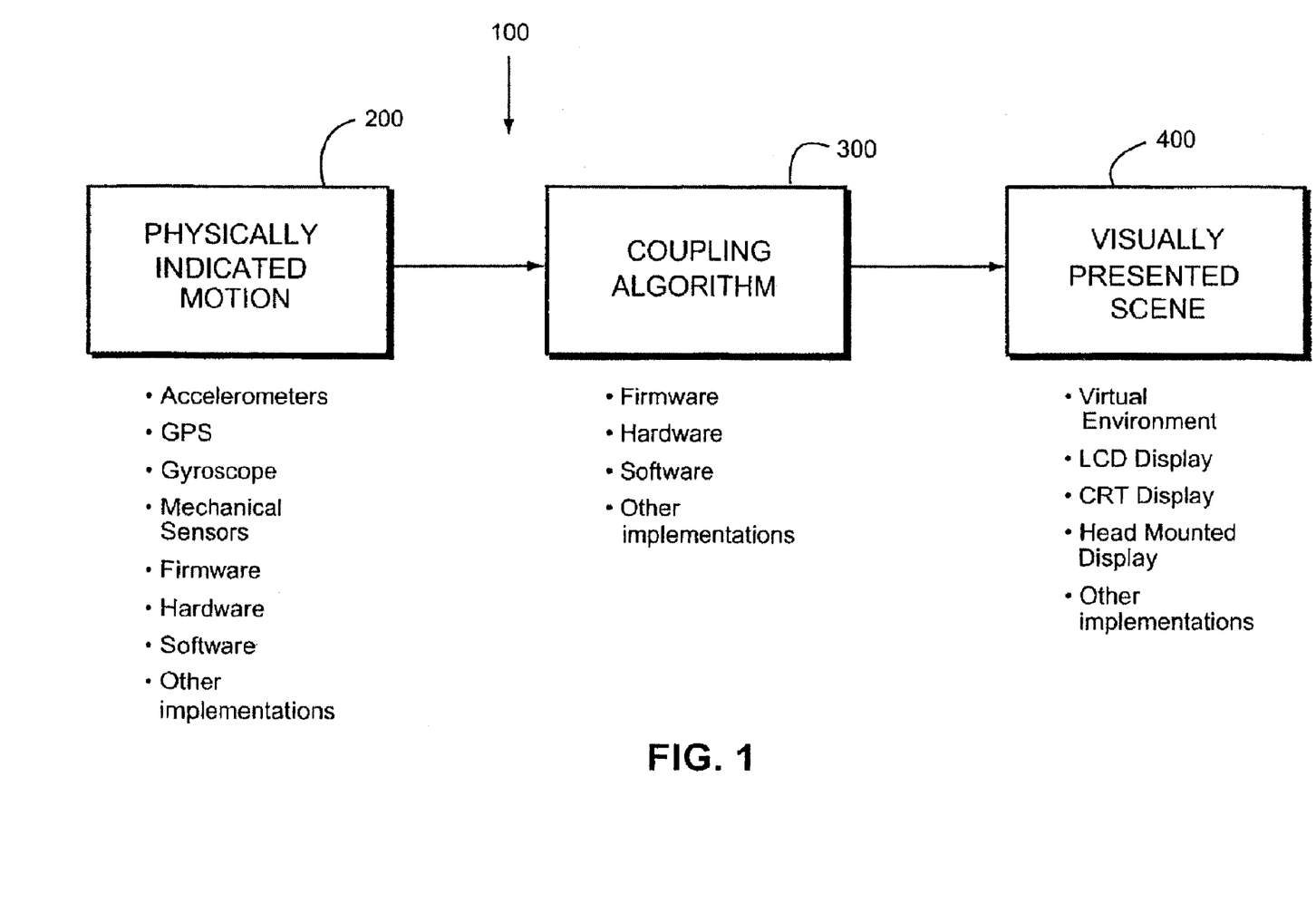
FIG. 1 depicts one example block diagram of a preferred non-limiting exemplary embodiment of a motion-coupled visual environment.

FIG. 1 shows an example non-limiting illustrative embodiment of a system 100 providing a motion-coupled visual environment. In the FIG. 1 example shown, system 100 includes three main components: a sensing arrangement 200 that detects the physically indicated motion, a coupling arrangement and associated algorithm 300 that couples the physically indicated motion and a presenting arrangement 400 that presents an evocative scene.

In the example embodiment, the sensing arrangement 200 includes one or more sensors that sense inertial motion. In one example embodiment, sensing arrangement 200 is disposed somewhere on the same platform carrying the person (e.g., mounted to a vehicle frame, vehicle floor, transport platform etc.). Sensing arrangement 200 can sense motion using any of a variety of different sensor types or combinations thereof, including for example:

accelerometer(s)
Global Positioning System (GPS)
Gyroscope(s)
Mechanical sensor(s)
Inclinometer(s)
vibration sensor(s)
altimeter(s)
optical-based sensor(s)
image-based sensor(s)
firmware
software
other implementations.

Motion sensing arrangement 200 provides an output to coupling arrangement 300. Coupling arrangement 300 in one example embodiment comprises firmware, hardware, software and/or other implementation that performs a coupling algorithm or method to derive one or more control parameters from the sensed motion. This derived control parameters is supplied to a presentation arrangement 400 that generates a visual scene for viewing by the person who may be subject to motion sickness. The scene presentation arrangement 400 may include for example:

virtual environment
liquid crystal display
cathode ray tube display
head mounted display
projection type display
holographic display
other implementations.

Many different configurations are possible. Four examples of system configurations are shown in FIG. 2 through FIG. 5.

Figure 2:
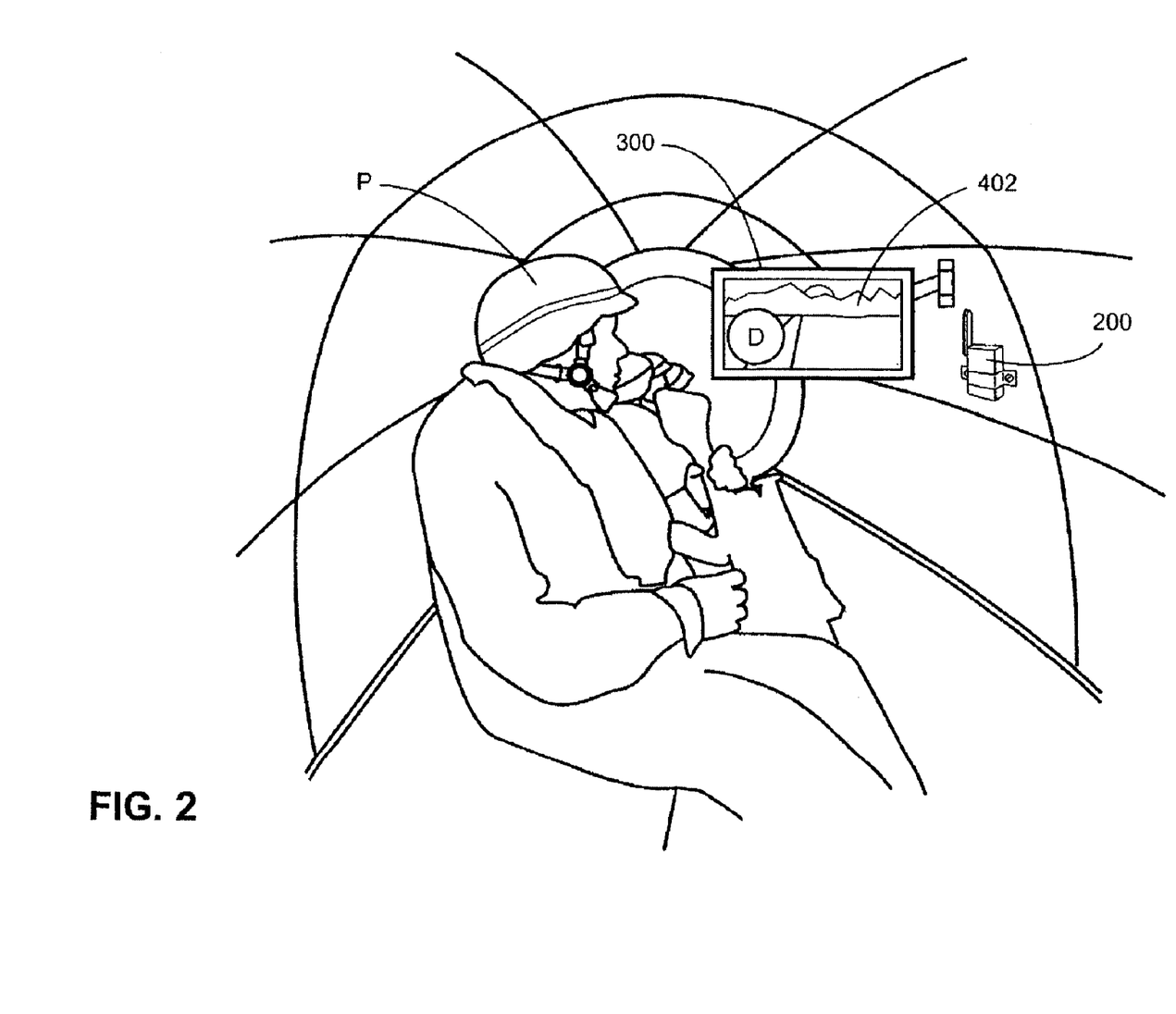
FIG. 2 depicts an example of use of the FIG. 1 system by a soldier in an aircraft.

In FIG. 2, a passenger (P) is shown viewing a computer-generated scene shown on a flat-panel display (D). The scene is being modified by coupling arrangement 300 to incorporate elements of the inertial environment that are sensed via a sensing arrangement 200. A corresponding motion-coupled virtual environment is presented on a display 402.

Figure 3:
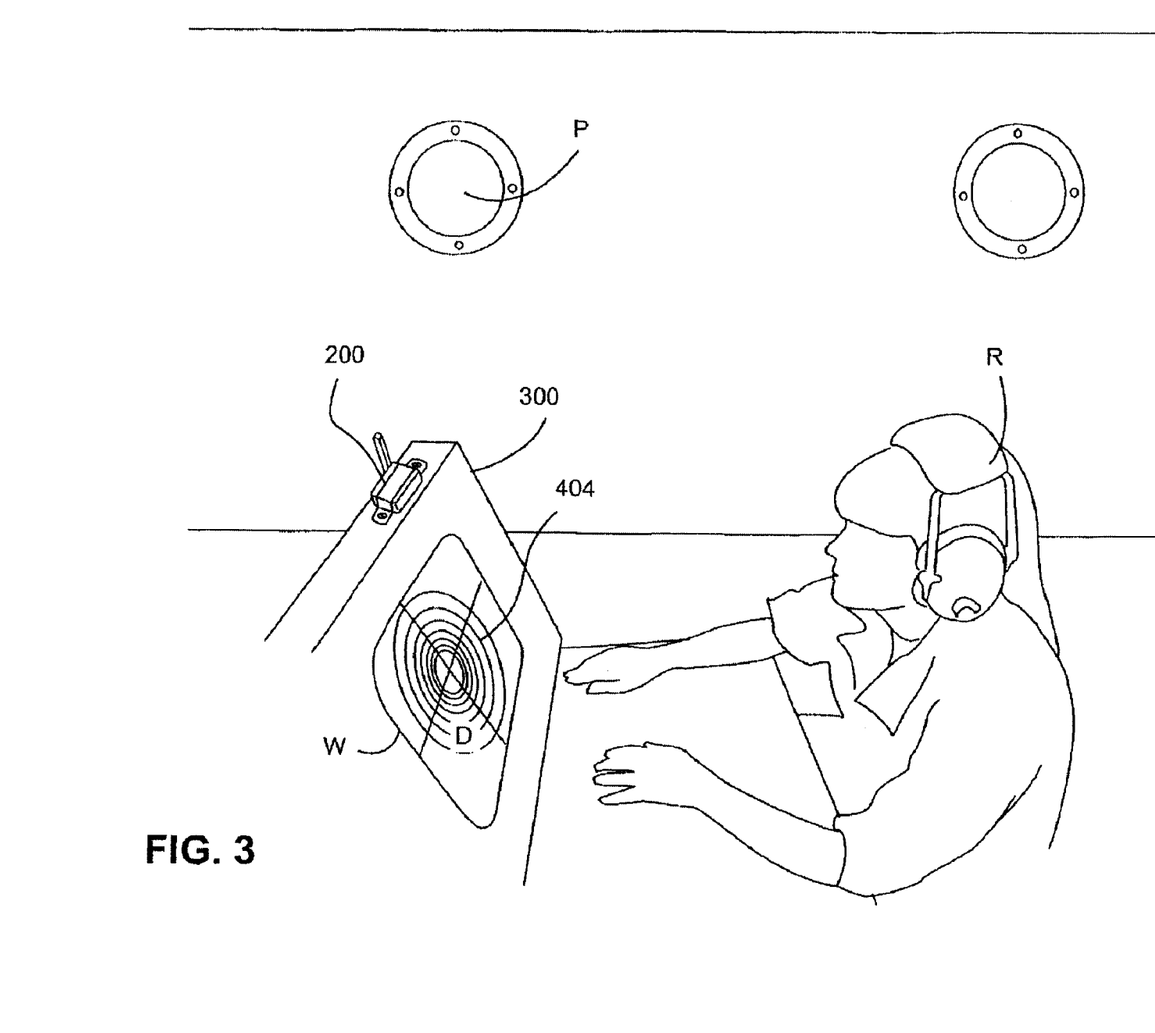
FIG. 3 depicts an example of use of the FIG. 1 system by a radar systems operator.

In FIG. 3, a radar systems operator R is shown viewing an electronic display 404. The display D is encapsulated within a window W that is moved by coupling arrangement 300 to incorporate elements of the inertial environment as sensed by sensor 200. Even though the operator R could have some access to the external environment through porthole P in this example, this is immaterial since his or her attention is focused elsewhere (i.e., on the display D).

Figure 4:
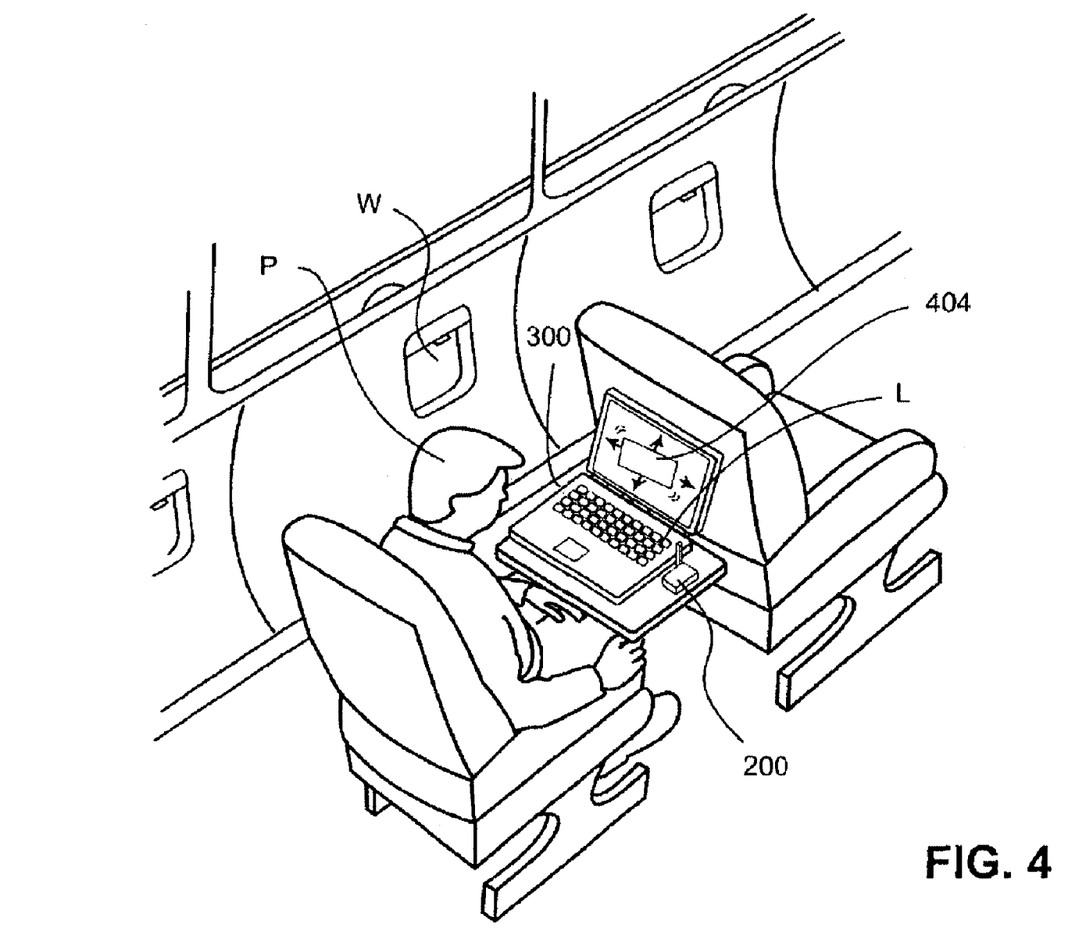
FIG. 4 depicts an example of use of the FIG. 1 system by a passenger on a commercial flight.

In FIG. 4, a passenger P on an aircraft is shown using a laptop computer L having a display 406. The computer L is shown displaying on display 404 a window of graphic/test information. The laptop runs software providing a coupling arrangement 300 that manipulates the window location to better correspond with the inertial environment as sensed by sensor 200. Although the passenger has access to an external view through a window (W), his or her attention is focused on the laptop or the external view may not be sufficiently evocative due to weather or lack of visual cues.

Figure 5:
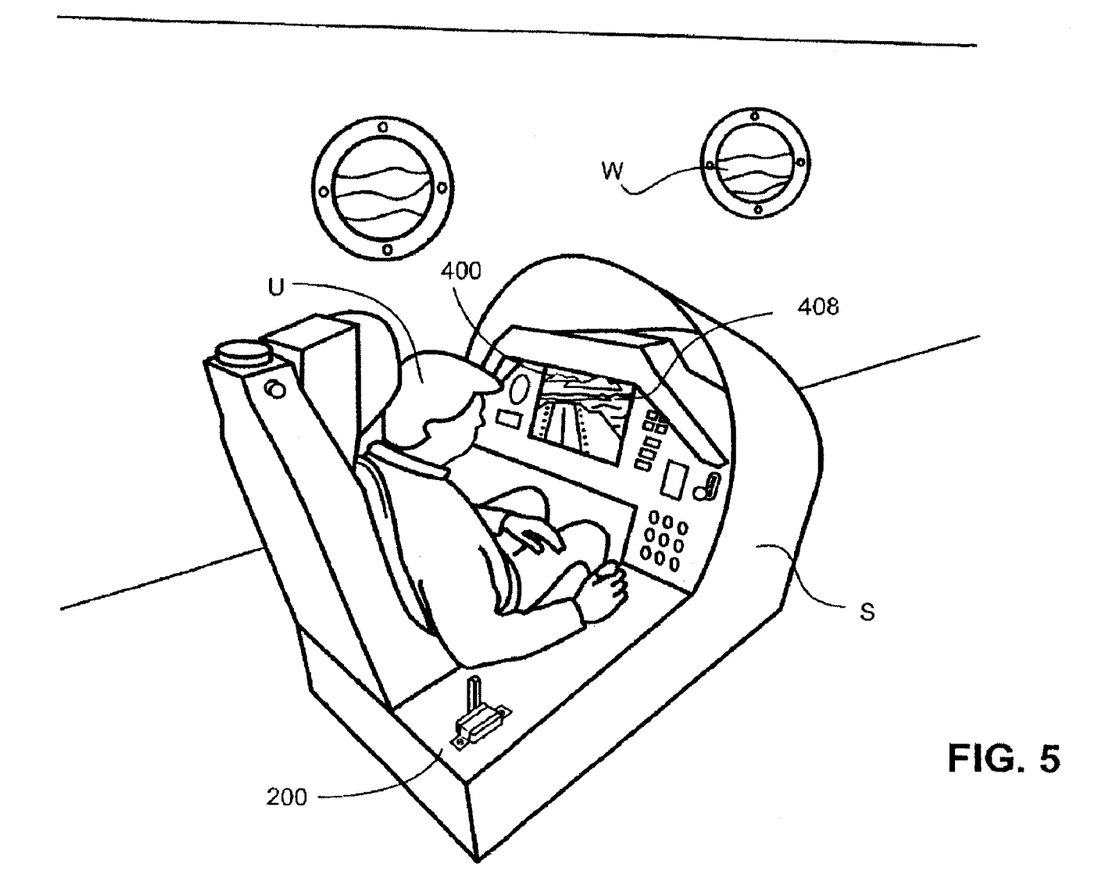
FIG. 5 depicts an example of use of the FIG. 1 system by a subject in a simulator.
Figure 6A:
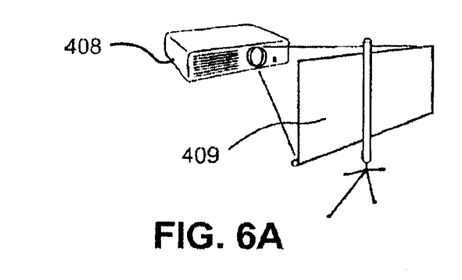
FIGS. 6A–6E depicts several exemplary displays.
Figure 6B:
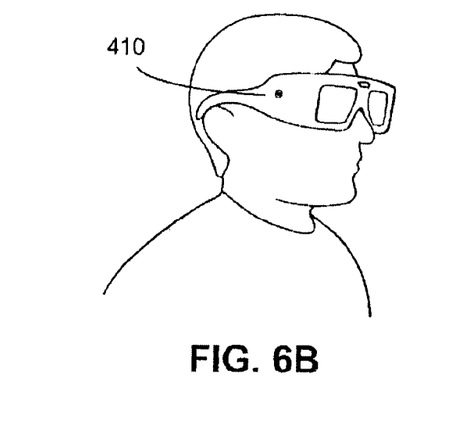
Figure 6C:
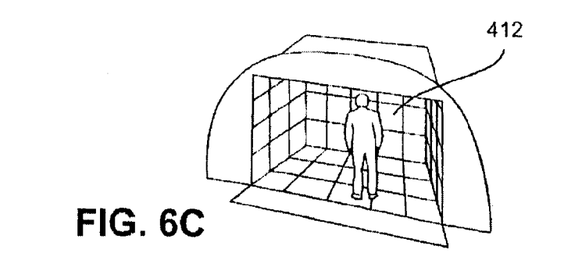
Figure 6D:
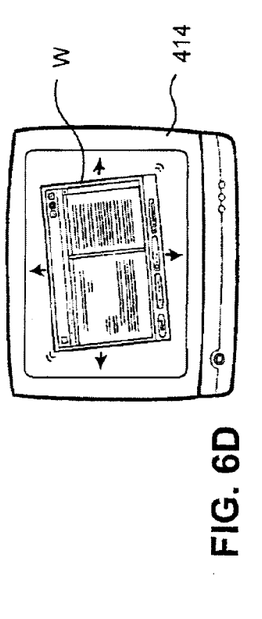
Figure 6E:
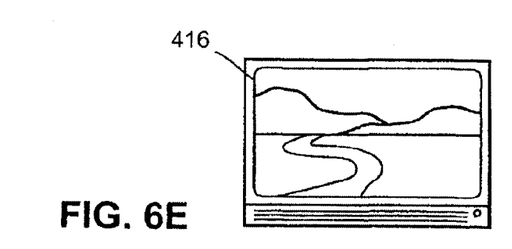

In FIG. 5, a user (U) is using a simulator S for training. He or she is presented with an immersive virtual environment via an electronic display 408. The user's perspective within this virtual environment is modified by system 100, of which the sensor package 200 is shown. Again, reference to an external environment (W) is not of any utility in this example.

Many types of displays are possible. Some examples are shown in FIGS. 6A–6E. A projector 408 may display either digital signals from a computer or television images onto a screen 409. A virtual environment may be displayed using a Head Mounted Display (HMD) 410, a projected virtual environment such as a CAVE 412 or some other means. A CRT or flat panel display 414 may also be used to show an immersive scene or other information window (W). A conventional television 415 can be used to display a windowed image that could be text, graphics or a combination. Many other display types are also possible.

There are a multitude of sensors and methods that can be used to monitor the inertial environment, as well as acquiring and processing the information. For any such system, the motion data would consist of some combination of translational and the rotational degrees of freedom. In most applications it will be sufficient to track the inertial components for the physically indicated motion produced by the environment. These inertial components are the main contributor to motion sickness.

One example of a sensor arrangement 200 is an array of three orthogonal accelerometers. Especially for slower moving platforms, such as a ship, pitch and roll may be approximated by sensing off-axis angles to the gravity normal vector, and heave, defined as vertical translation parallel to the gravity normal, may be calculated via a double integration of acceleration or via some other means.

For faster moving platforms, such as an automobile or aircraft, it is sometimes desirable to sense further degrees of freedom to estimate horizontal degrees of freedom and the yaw component. This may be done, for example, by using gyroscopes or rate gyroscopes to measure rotational degrees of freedom, freeing the accelerometers or other measurement device to sense translational information.

Figure 7:
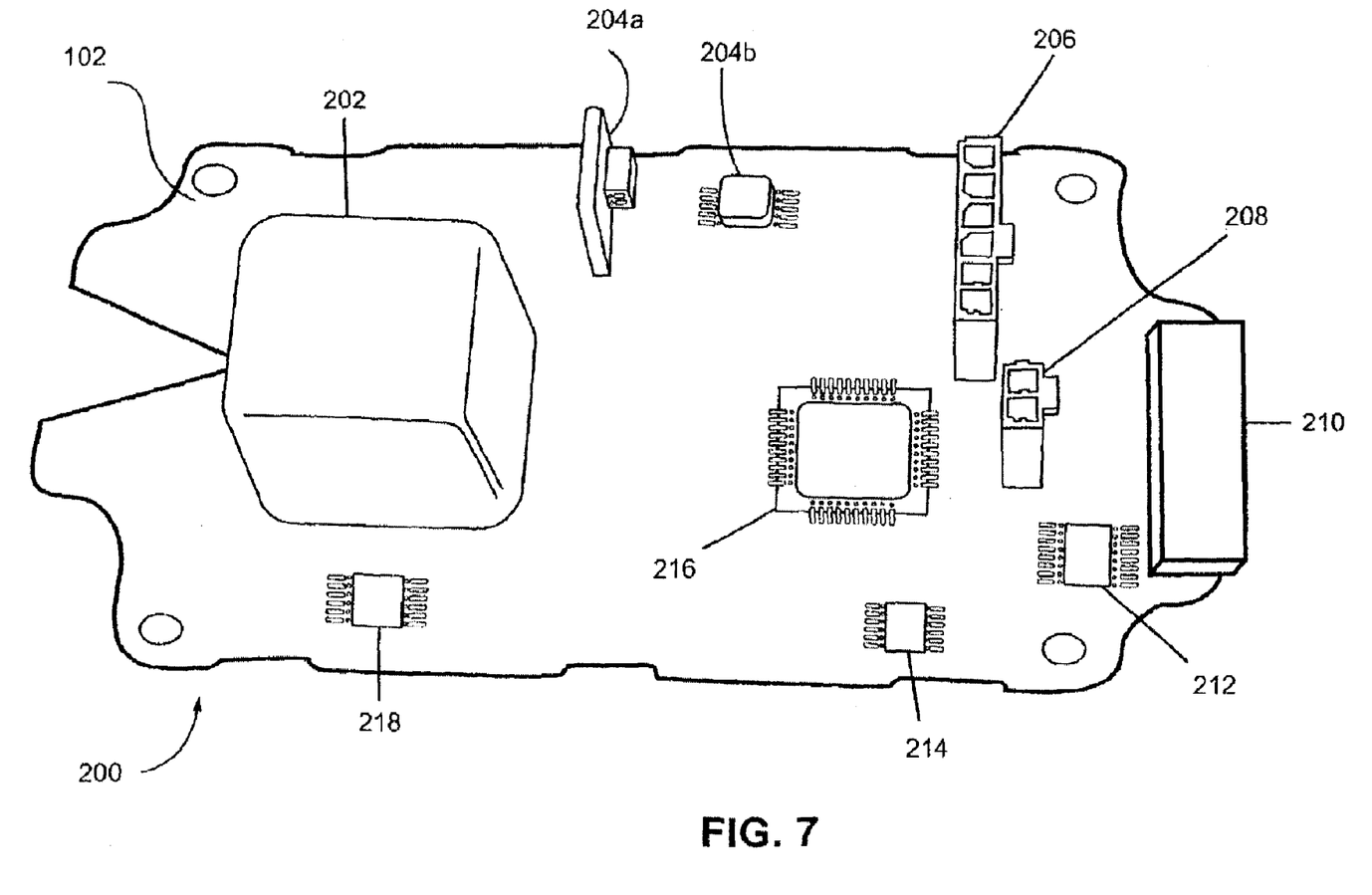
FIG. 7 depicts a perspective physical view of an exemplary electronics hardware layout.

In general, an implementation of sensor arrangement 200 for acquiring the physically indicated inertial motion can combine accelerometers, gyroscopes, GPS, other sensors, and information processors. An illustrative example of such an implementation is depicted in FIG. 7. Here, a processor board 102 indicates a gyroscope 202, an Analog Devices ADXL202 accelerometer chips 204a, 204b, a LED and switch connector 206, a battery connector 208, an RS232 or other serial port connector 210, a RS232 converter 212, a SEEPROM 214, a PIC 16C73 8 bit microcontroller 216 and operational amplifiers 218. In the example, the sensor arrangement 200 is mounted to the motion platform with minimal mechanical compliance such that the data acquired matches the motion experienced. For more accurate motion data, the sensor should be placed in proximity to the user or users with known relative orientation. It may be calibrated to establish relative directions of motions such as front, back, left, right, etc. with respect to the user. This calibration may either take place in the factory, implying that the system is to be oriented to the user is a set manner, or it may take place at the point of use.

Figure 8:
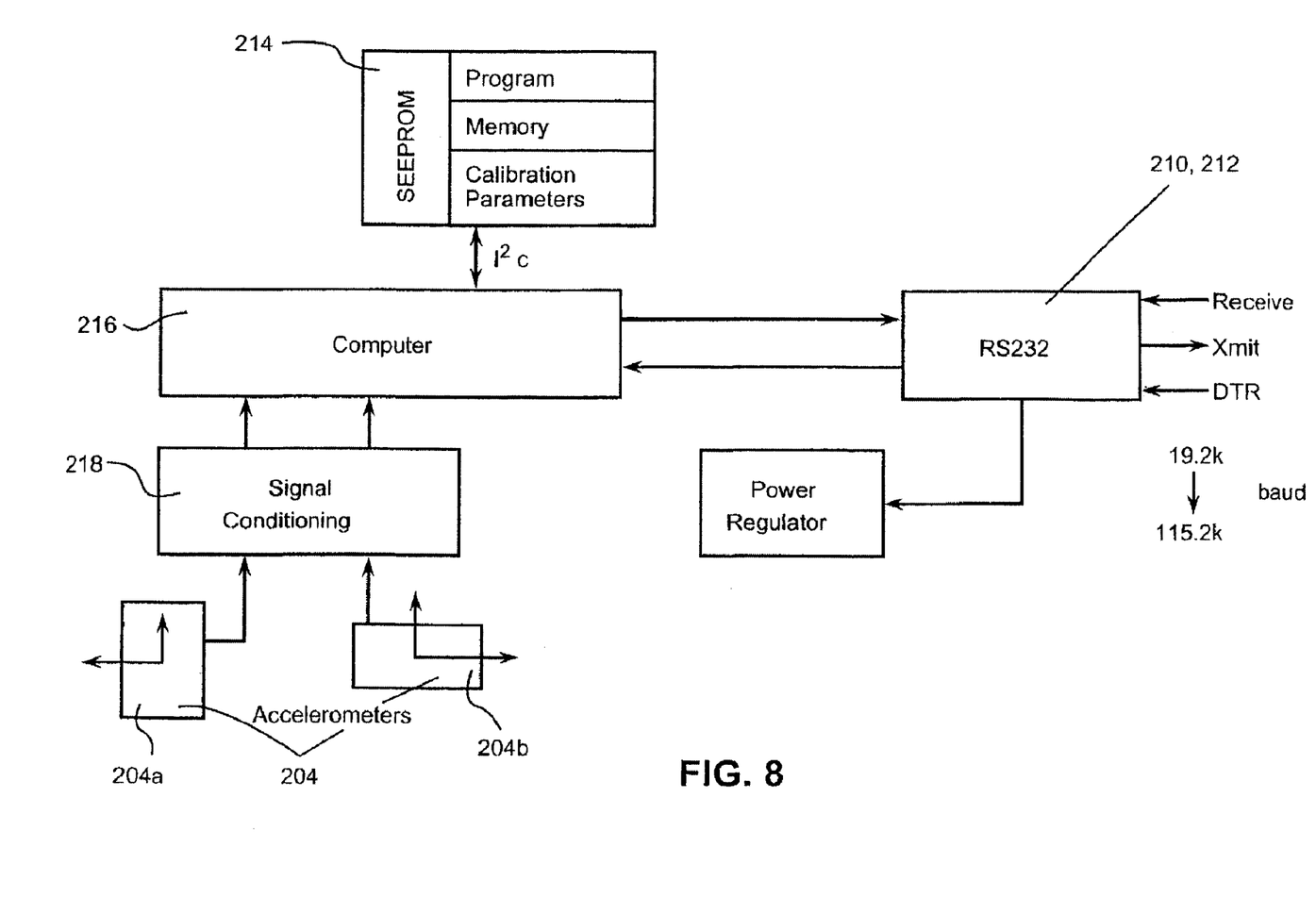
FIG. 8 depicts a block diagram of an exemplary electronics hardware functional diagram.

FIG. 8 shows an example block diagram of an illustrative non-limiting sensor arrangement 200. Accelerometers 204 or other sensors record inertial frame reference data. These data are processed by signal conditioning hardware 218 before being input to a computer 216, normally a microcontroller or microprocessor. The computer 216 communicates with a SEEPROM memory device 214 or other memory device, which stores programming code, calibration parameters and run-time and other data in memory, or the computer 216 may use its own internal memory. The computer 216 also interacts with an RS232 serial communications system 210, 212 or other communications system that is often power regulated to better interface with external devices. The communications system 210, 212 transmits and receives information at a variety of baud rates.

Figure 9:
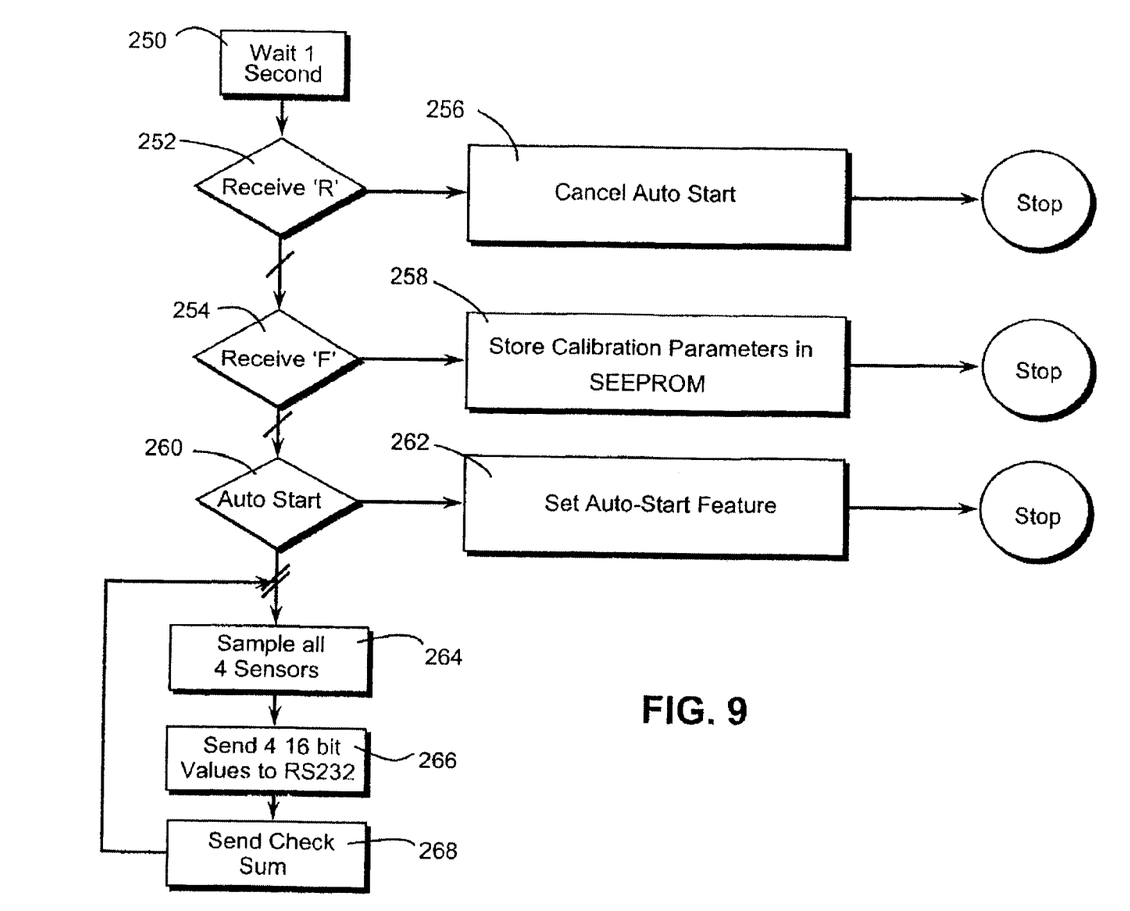
FIG. 9 depicts an exemplary embedded system software flowchart.

The electronics hardware is often controlled by software embedded into various devices on the hardware such as the microcontroller 216 and other devices. FIG. 9 shows one example of how this software may operate although many other configurations are possible. Once system 100 is turned on, the software begins an autostart function by waiting a set period (block 250). After this period is complete, the system 100 checks to see of its registers have received a command from the offboard system such as an "R" or a "F" (blocks 252, 254). These commands, for example, would indicate that the system 100 should perform other functions (blocks 256, 258) before stopping the loop. Likewise, if the AutoStart mode fails (decision block 260), the system will attempt to recover (block 262) before stopping. Assuming that the system starts successfully, it will sample the sensors (block 264), communicate data to an output port (block 266) and send check sums to the microcontroller that uses these data to check for errors (block 268). After completing these tasks, the system will loop back to sampling the sensors again.

An example of the motion coupling arrangement 300 provides an algorithm that takes selected vectors of the physically indicated motion and generates appropriate visual scene information. The appropriate coupling algorithm may be different for different individuals. Recent research has shown that humans often perceive their inertial environment incorrectly when they lack any or sufficient visual cues. Since it is the perceived inertial environment that must be rationalized with the perceived visual environment, even a perfect match of inertial and visual environments may still cause motion sickness. In these cases, it is possible to test the user in a well-controlled motion environment and record inaccurate tendencies of their proprioceptive receptors. For example, in testing subjects in a Vertical Linear Oscillator (VLO), only a small percentage of the population may be able to accurately perceive their motion. Of the majority of humans tested, a large number experienced a stable and predictable error in perception. Other subjects, however, perceive the inertial environment as changing. For the subjects perceiving a stable environment, an exemplary instantiation may be calibrated to individual inertial sensing predilections, thus greatly accentuating the effectiveness of the system in relieving motion sickness.

In addition to calibration beforehand, another possible embodiment would allow for passive and non-passive feedback/control from the user. The physiological effects of motion sickness are well documented and can be monitored. Using this physiological feedback, such as heart rate and/or perspiration and/or pupil dilation etc., the coupling algorithm would adjust to the individual. In addition, individuals can be provided with controls that allow them to adjust various parameters of the coupling algorithm, such as magnitude or motion profile of the physically indicated motion.

Figure 10:
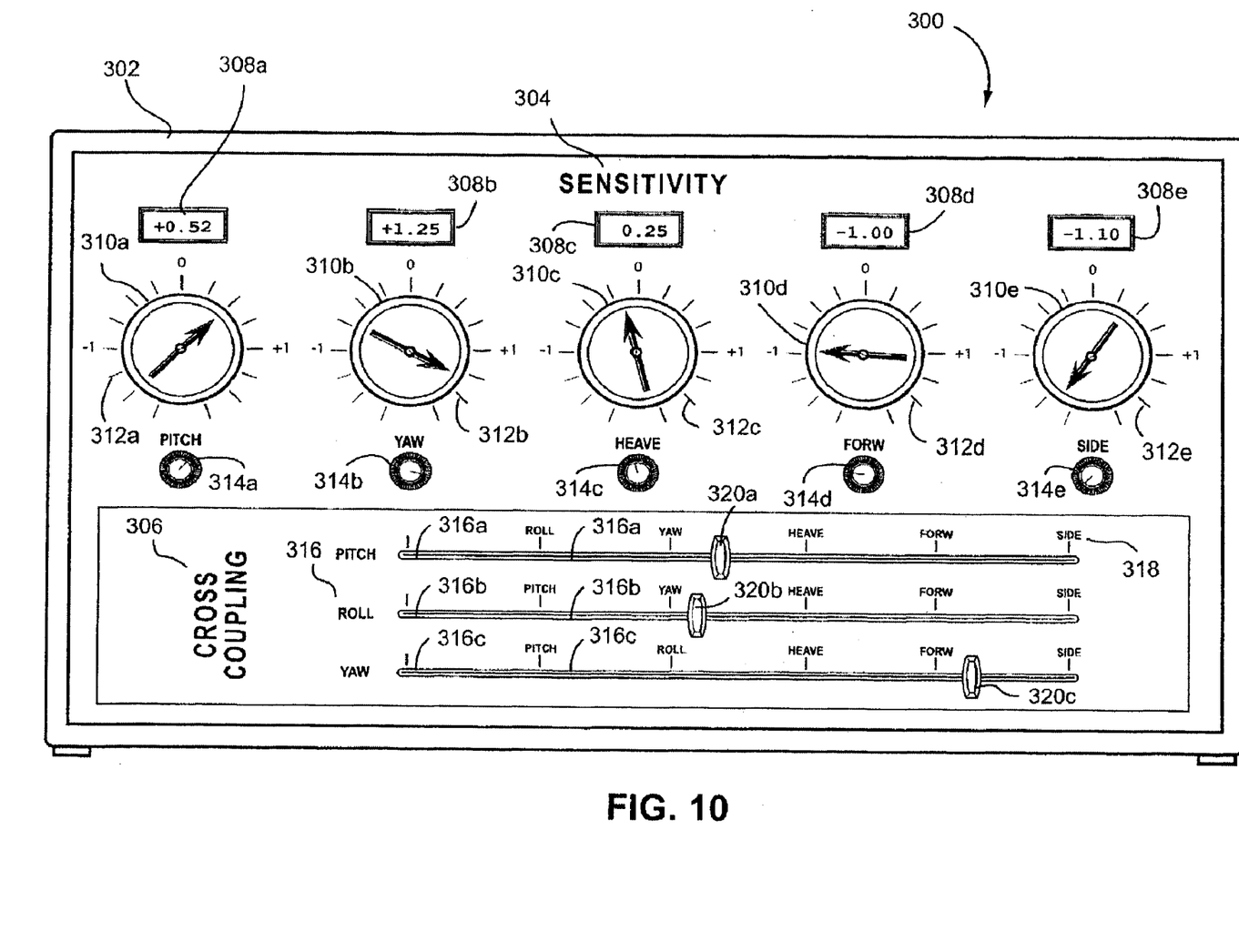
FIG. 10 depicts an example user control interface for adjusting parameters such as yaw, pitch, roll, and heave among many other possible parameters.

An example of one coupling arrangement 300 is depicted in FIG. 10, although other instantiations are possible. Such controls could be mechanical in nature, a graphical user interface (GUI) or some other means. FIG. 10 depicts a mechanical control panel 302. There are two sections of control: Sensitivity section 304 and Cross Coupling section 306. The sensitivity section 304 controls the mapping of a given degree of freedom from the inertial reference frame to the visual. For example, an indicator 308 of +0.52 for pitch would imply that the pitch output is 52% of that input. Example digital readouts 300 are shown. Analog readings by the dials 310 as they point to gradated markings 312 are also possible. The user may control these sensitivity channels via knobs 314 or some other interface. Cross coupling section 306 provides several channels such as roll 316 indicating the mapping from one inertial degree of freedom onto a different visual degree of freedom. For example, roll channel 316 could map partially onto yaw and heave or other degree of freedom as indicated on a scale 318 using, for example, a slide bar 320. In general, great care should be taken in making these modifications. Recent experiments have shown that some cross couplings are beneficial, while others are counterproductive. The user interface does not need to be mechanical; it can be a graphical user interface on a computer, voice activated or many other types of interface or the coupling parameters can be preprogrammed or preset and the user interface eliminated altogether. The FIG. 10 arrangement shows a flexible interface providing many different types of couplings and cross-couplings, but other embodiments can be substantially simpler and more constrained.

The coupling arrangement 300 can be implemented through hardware, software, or combination of the two. For example, hardware may be used for signal processing and conditioning, and may be complemented with firmware and software to modify and generate appropriate coupling output. In this example, the hardware provides for fast signal processing, while the firmware and software provide flexibility and a readily available interface.

Figure 11:
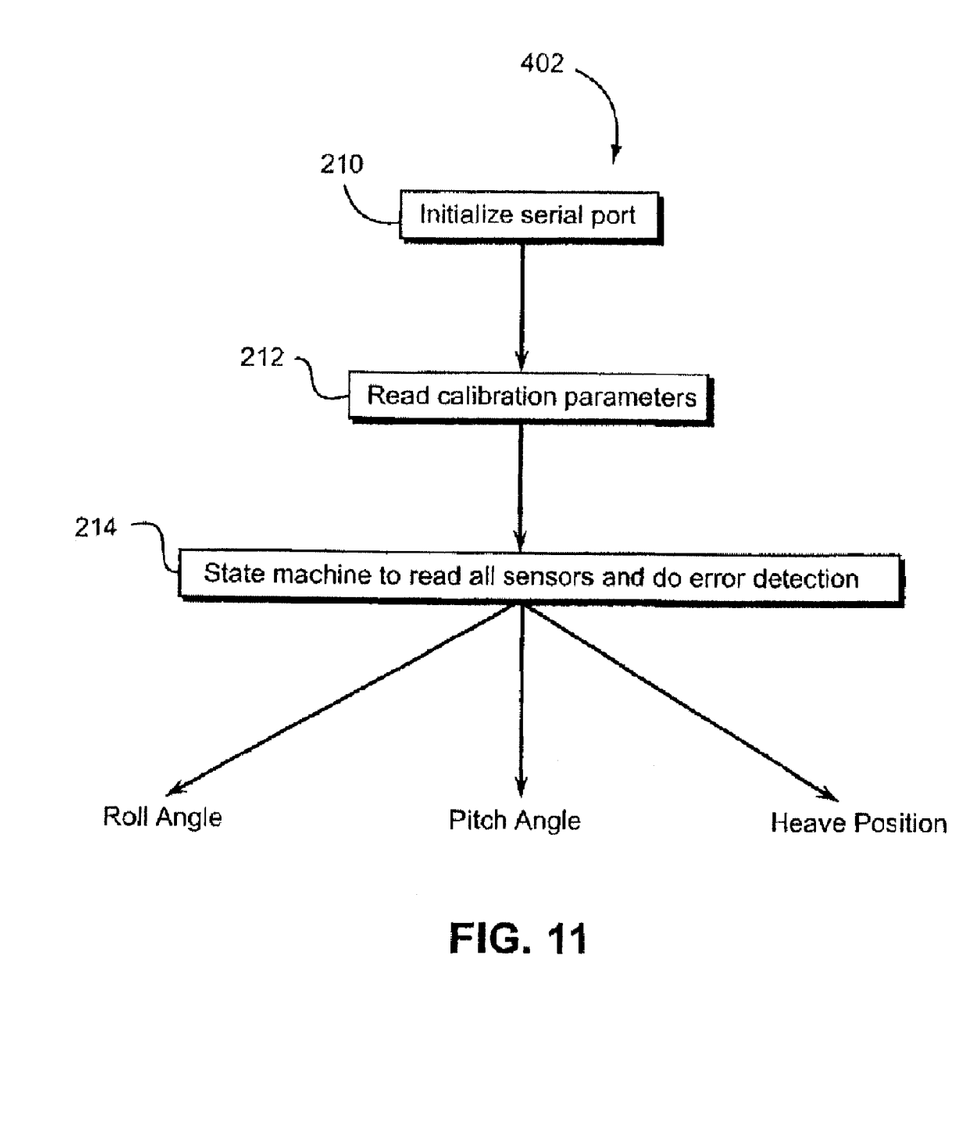
FIG. 11 depicts an exemplary flowchart for device driver software.

The display arrangement 400 will often be interfaced to the hardware via software oftentimes called a "device driver." One example of such software is shown in FIG. 11. Once the exemplary display program is first opened, it begins by initializing communications with the sensor arrangement 200 through an interface such as a serial port 210 (block 404). It will then read calibration data as in 212 that are installed either at the factory or set via the supplied user interface (block 406). The software then enters a continuous loop block 214 where it is continuously reading sensor data provided by the hardware and adjusts the values for input to higher-level display software as required by the calibration parameters and other data and algorithms (block 408).

The exemplary embodiment of system 100 may be implemented using a preset algorithm for mapping inertial motion to the visual scene, or the user may modify the mapping for personal preference using either a mechanical or graphical user interface. Furthermore, the exemplary presentation arrangement 400 in certain applications does not necessarily generate an image that realistically portrays the direction of inertial motion sensed by sensor arrangement 200. For example, it may not always be possible or even desirable for an essentially two-dimensional information display such as a radar screen, a television program, or a computer text document display to accurately depict inertial motion sensed in three-dimensions. One example mapping algorithm maps inertial heave information to display motion in the pitch direction. Human subject experiments have shown that while subjects can easily perceive heave, a physically correct representation of heave in the visual environment is only rarely visually stimulating to a sufficient degree to produce the necessary correlation between visual and inertial environments. Therefore, exemplary illustrative embodiments of system 100 may map sensed inertial heave into the visual pitch direction, normally adjusting pitch motion to remain within 10 degrees of throw or some other range of motion. We find this produces much better results for at least some applications in terms of subjects sensing a correlation between visual and inertial environments. While the invention has been described in connection with what is presently considered to be the most practical and preferred embodiment, it is to be understood that the invention is not to be limited to the disclosed embodiment, but on the contrary, is intended to cover various modifications and equivalent arrangements included within the scope of the appended claims.

We claim:

1. A method for preventing, reducing or treating motion sickness of a user on a moving platform, comprising:
   sensing at least one inertial motion condition existing on said moving platform and providing signals responsive thereto;
   processing said signals to provide display control signals; and
   displaying, on a surface having first and second dimensions, at least one window for the user to focus on, and moving, based at least in part on said display control signals, the displayed position of said at least one window on said surface in both said first and second dimensions so as to correlate perceived motion with said sensed inertial motion.

2. The method of claim 1 wherein said displaying comprises displaying an evocative scene.

3. The method of claim 1 wherein said sensing comprises sensing acceleration in plural directions.

4. The method of claim 1 wherein said sensing includes sensing changes in orientation relative to the earth.

5. The method of claim 1 wherein said signal providing includes conditioning said sensed inertial motion to provide corresponding representative digital signals.

6. The method of claim 1 further including cross-coupling different aspects of said sensed inertial motion.

7. The method of claim 1 wherein further including applying a coupling algorithm that has been empirically customized for a particular human subject.

8. The method of claim 1 wherein said surface comprises a computer screen, and said displaying comprises displacing said window displayed on said computer screen.

9. The method of claim 1 wherein said surface comprises a television screen, and said displaying comprises displacing an entertaining image displayed on a television screen.

10. A system for preventing, reducing or treating motion sickness of a user on a moving platform, said system comprising:
    at least one inertial sensor mechanically coupled to said moving platform, said inertial sensor sensing at least one inertial motion conditions existing on said moving platform and providing signals responsive thereto;
    a processing arrangement connected to receive said signals, said processing arrangement processing said signals to provide display control signals; and
    a display device connected to receive said display control signals, said display device providing a two-dimensional display on a surface having first and second dimensions, said display device displaying at least one window for the user to focus on, said display device moving, based at least in part on said processing performed by said processing arrangement, the displayed position of said at least one window on said surface in both said first and second dimensions so as to correlate said perceived motion with said sensed inertial motion.

11. The system of claim 10 wherein said display comprises a television screen.

12. The system of claim 10 wherein said display comprises a head-mounted display.

13. The system of claim 10 wherein said display comprises a projection type display.

14. The system of claim 10 wherein said display comprises a computer screen.

15. The system of claim 10 wherein said sensor includes an accelerometer.

16. The system of claim 10 further including signal processing circuitry that cross-couples plural sensed inertial motion signals.

17. In a system for preventing, reducing or treating motion sickness of a user on a moving platform, the system including a sensor for sensing at least one inertial motion condition existing on said moving platform, and a processor coupled to the sensor that processes said sensed inertial motion condition to provide display control signals for coupling to a display of the type that provides a display surface having first and second dimensions, said display displaying at least one window for the user to focus on, a memory device storing instructions for execution by said processor, said instructions causing the processor to move the displayed position of said at least one window on said display surface in both said first and second dimensions so as to correlate perceived motion with said sensed inertial motion.

\* \* \* \* \*